United States Patent [19]
Thompson

[11] Patent Number: 5,919,771
[45] Date of Patent: Jul. 6, 1999

[54] UREA AND THIOUREA DERIVATIVES OF GLYCOPEPTIDES

[75] Inventor: Richard Craig Thompson, Frankfort, Ind.

[73] Assignee: Eli Lilly and Company, Indianapolis, Ind.

[21] Appl. No.: 09/070,219

[22] Filed: Apr. 30, 1998

Related U.S. Application Data

[60] Provisional application No. 60/047,196, May 20, 1997.

[51] Int. Cl.$^6$ .......................... A61K 31/71; A61K 38/12; A61K 38/14
[52] U.S. Cl. .................................. 514/27; 514/9; 514/43; 530/317; 536/7.1; 536/29.1
[58] Field of Search .................................. 514/9, 27, 43; 530/317; 536/7.1, 29.1

[56] References Cited

U.S. PATENT DOCUMENTS

| | | | |
|---|---|---|---|
| 4,643,987 | 2/1987 | Nagarajan et al. | 514/8 |
| 4,698,327 | 10/1987 | Nagarajan et al. | 514/8 |
| 5,534,420 | 7/1996 | Debono et al. | 435/71.3 |
| 5,591,714 | 1/1997 | Nagarajan et al. | 514/9 |
| 5,602,229 | 2/1997 | Malabarba et al. | 530/317 |
| 5,843,889 | 12/1998 | Cooper et al. | 514/8 |

FOREIGN PATENT DOCUMENTS

| | | |
|---|---|---|
| 0 435 503 A1 | 7/1991 | European Pat. Off. . |
| 0 667 353 a1 | 1/1995 | European Pat. Off. . |
| WO 96/30401 | 10/1996 | WIPO . |
| 98/00153 | 1/1998 | WIPO . |

OTHER PUBLICATIONS

*J. Chem. Soc., Chem. Comm.*, Williams et al. 1694–1695 (1987).
*J. Chem Soc. Chem. Comm.*, Nagarajan, et al. 1306–1307 (1988).
*J. Antibiotics*, Pavlov, et al. vol. 46, No. 11, 1731–1739 (1993).
*J. Antibiotics*, Cristofaro, et al. vol. 48. No. 8, 805–810 (1995).
Poster at ASM Meeting, Grissom–Arnold, New Orleans, May 19–23, 1996.
*Microbial Drug Resistance*, Grissom–Arnold, 3, 53–64 (1997).
Antibiotics Chemotherapy, vol. 34, No. 5, 352–358 (1989).
*J. Chem Soc. Perkin. Trans. I*, Williams, 2335–2339 (1989).
*J. Antibiotics*, Miroshnikova et al, vol. 49, No. 11, 1157–1161 (1996).
*J. Natural Products*, Zmijewski, et al, vol. 52, No. 1, 203–206 (1989).
*J. Antibiotics*, Cristofarao, et al, vol., 48, No. 8, 805–810 (1995).

*Primary Examiner*—Howard C. Lee
*Attorney, Agent, or Firm*—Kathleen R. S. Page; James J. Sales

[57] ABSTRACT

The present invention is directed to $N^{LEU}$-carbamoyl and thiocarbamoyl derivatives of A82846B and $N^{DISACC}$ variations thereof. These derivatives are useful as antibacterials and also as starting materials from which further antibacterial compounds are prepared.

9 Claims, No Drawings

UREA AND THIOUREA DERIVATIVES OF GLYCOPEPTIDES

This application claims priority to provisional application Ser. No. 60/047,196 dated May 20, 1997.

BRIEF SUMMARY OF THE INVENTION

The present invention is directed to $N^{LEU}$-carbamoyl and thiocarbamoyl derivatives of A82846B and $N^{DISACC}$ variations thereof. These derivatives are useful as antibacterials and also as starting materials from which further antibacterial compounds are prepared.

DETAILED DESCRIPTION OF THE INVENTION

The present invention is directed to compounds of the formula

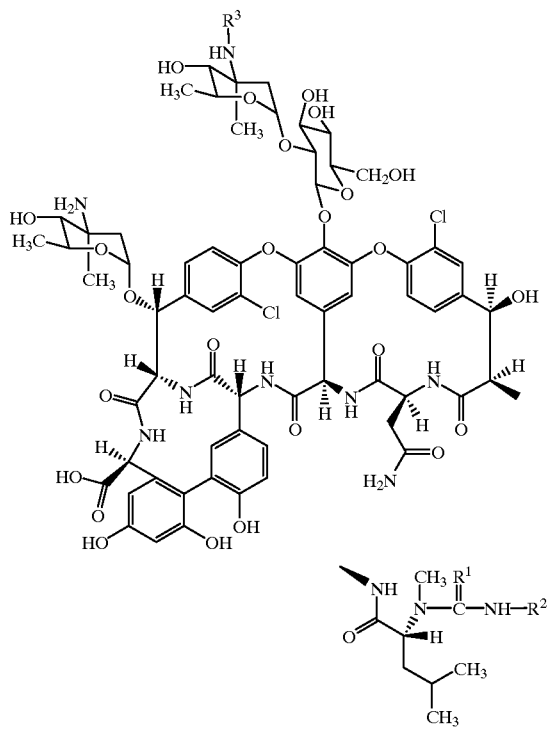

wherein $R^1$ represents O or S;
$R^2$ represents
  alkyl of $C_1$–$C_{10}$,
  phenyl,
  naphthyl, or
  phenyl substituted by one or two substituents, each of which is independently halo, loweralkyl of $C_1$–$C_4$, loweralkoxy of $C_1$–$C_4$, benzyloxy, nitro, or

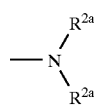

wherein each $R^{2a}$ is independently loweralkyl of $C_1$–$C_4$; and $R^3$ represents hydrogen or —$CH_2$—$R^{3a}$ wherein $R^{3a}$ represents
  alkyl of $C_1$–$C_{11}$,
  alkyl of $C_1$–$C_{11}$—$R^4$, or
  $R^4$-$(0_{(0\ or\ 1)}$—$R^4)_{0\ or\ 1}$,
wherein each $R^4$ is independently phenyl or phenyl substituted by one or two substituents, each of which is independently halo, loweralkyl of $C_1$–$C_4$, loweralkoxy of $C_1$–$C_4$, or loweralkylthio of $C_1$–$C_4$, and pharmaceutically acceptable salts thereof.

The compounds of the present invention are prepared by reacting a parent glycopeptide of the formula

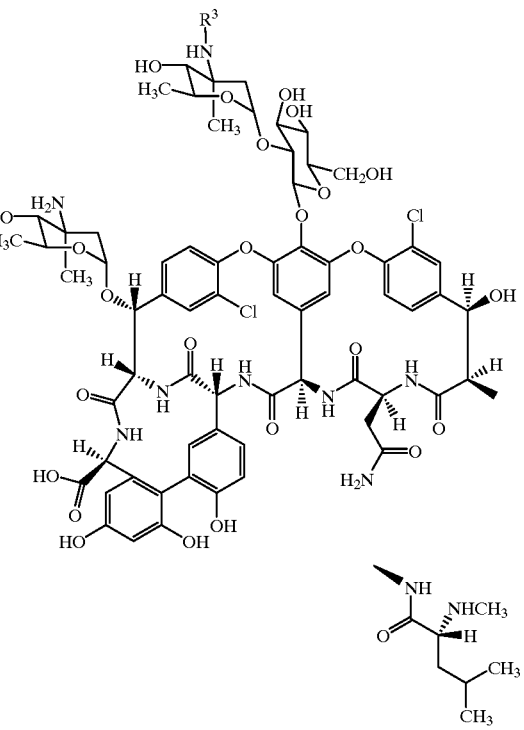

wherein $R^3$ is as defined above, with an isocyanate or isothiocyanate of the formula $R^1CN$—$R^2$, wherein $R^1$ and $R^2$ are as defined above. This is the first step of the so-called Edman degradation, which is a two-step process for the cleavage of the N-terminal residue of a peptide or protein.

The reaction to prepare the present compounds is carried out in a polar solvent, such as water, in the presence of an organic base, such as pyridine. Generally the reaction is carried out at a temperature of about 15° C. to about 35° C. for one to five hours. The reaction is preferably carried out at a temperature from about 25° C. to 30° C. for one to two hours, in water with pyridine as the base. The reaction consumes equimolar amounts of the reactants but a slight excess of the isocyanate or isothiocyanate is preferred. The product is separated and purified if desired in conventional procedures. When it is desired, a salt can be prepared in standard procedures.

The following examples illustrate the preparation of the compounds of the present invention.

PREPARATION OF COMPOUND OF EXAMPLE 22

$N^{DISACC}$-(p-(p-Chlorophenyl)benzyl)A82846B trihydrochloride (100.0 mg, 0.0526 mmol) was dissolved in 10 ml $H_2O$-pyridine (1:1 v/v) and treated with phenyl isothiocyanate (0.010 ml, 0.083 mmol). The resulting mixture was stirred at room temperature for 1 hour at which time HPLC analysis indicated complete consumption of the starting material. The reaction mixture was concentrated in vacuo and the crude product was purified by preparative HPLC to give 76.6 mg (76% yield) of $N^{LEU}$-(phenylthiocarbamoyl)-$N^{DISACC}$-(p-(p-chlorophenyl)benzyl) A82846B. FAB-MS: calc. For $C_{93}H_{102}Cl_3N_{11}O_{26}S$ 1925.5, obtained 1928.5 (M+3).

PREPARATION OF COMPOUND OF EXAMPLE 23

A82846B triacetate (270 mg, 0.157 mmol) was dissolved in 30 ml $H_2O$-pyridine (1:1 v/v) and treated with phenyl isocyanate (0.030 ml, 0.277 mmol). The resulting mixture was stirred at room temperature for 1 hour at which time HPLC analysis indicated complete consumption for the starting material. The reaction mixture was concentrated in vacuo and the crude product was purified by preparative HPLC to give 62.5 mg (23% yield) of $N^{LEU}$-(phenylcarbamoyl)-A82846B. FAB-MS: Calc. For $C_{80}H_{93}Cl_2N_{11}O_{27}$ 1709.6, obtained 1712.1 (M+3).

The HPLC procedures reported in these examples were as follows:

Analytical: Reactions were monitored by analytical HPLC using a Waters $C_{18}$ μBondapak or Novapak $C_{18}$ column (3.9×300 mm) and UV detection at 280 nm. Elution was accomplished with a linear gradient of 5% $CH_3CN$-95% buffer to 80% $CH_3CN$-20% buffer over 30 minutes. The buffer used was 0.5% triethylamine in water, adjusted to pH 3 with $H_3PO_4$.

Preparative: Crude reaction mixtures were purified by preparative HPLC using a Waters $C_{18}$ Nova-Pak column (40×300 mm) and UV detection at 280 nm. Elution was accomplished with a linear gradient of 5% $CH_3CN$-95% buffer to 80% $CH_3CN$-20% buffer over 30 minutes. The buffer used was 0.5% triethylamine in water, adjusted to pH 3 with $H_3PO_4$. The desired fractions were subsequently desalted with a Waters $C_{18}$ Sep-Pak (35 cc) followed by lyophilization.

Compounds were desalted as follows. A Waters Sep-Pak cartridge was pre-wet with methanol (2–3 column volumes) then conditioned with water (2–3 column volumes). The sample, dissolved in a minimum volume of water, was loaded onto the Sep-Pak column which was then washed with water (2–3 column volumes) to remove the unwanted salts. The product was then eluted with an appropriate solvent system, typically 1:1 $CH_3CN/H_2O$, $CH_3CN$, and/or methanol. The organic solvent component was removed in vacuo and the resulting aqueous solution lyophilized to give the final product.

Representative compounds of the present invention are listed in the following table:

TABLE I

| Ex # | Name | FAB-MS | M + X | Analytical HPLC, min |
|---|---|---|---|---|
| 1 | $N^{LEU}$-(PHENYLTHIOCARBAMOYL)A82846B | 1728.5 | 3 | 18.2* |
| 2 | $N^{LEU}$-(PHENYLTHIOCARBAMOYL)-$N^{DISACC}$-(p-CHLOROBENZYL)A82846B | 1852.3 | 3 | 21.4* |
| 3 | $N^{LEU}$-(PHENYLTHIOCARBAMOYL)-$N^{DISACC}$-(p-PHENOXYBENZYL)-A82846B | 1911.0 | 3 | 23.6* |
| 4 | $N^{LEU}$-(PHENYLTHIOCARBAMOYL)-$N^{DISACC}$-(p-PHENYLBENZYL)A82846B | 1894.5 | 3 | 23.2* |
| 5 | $N^{LEU}$-(1-NAPHTHYLTHIOCARBAMOYL)A82846B | 1778.5 | 3 | 19.8* |
| 6 | $N^{LEU}$-(1-NAPHTHYLTHIOCARBAMOYL)-$N^{DISACC}$-(p-CHLOROBENZYL)A82846B | 1902.5 | 3 | 15.4* |
| 7 | $N^{LEU}$-(1-NAPHTHYLTHIOCARBAMOYL)-$N^{DISACC}$-(p-PHENOXYBENZYL)A82846B | 1960.6 | 3 | 17.1* |
| 8 | $N^{LEU}$-((p-CHLOROPHENYL)-THIOCARBAMOYL)A82846B | 1763.0 | 4 | 20.5* |
| 9 | $N^{LEU}$-((p-METHOXYPHENYL)-THIOCARBAMOYL)A82846B | 1757.3 | 2 | 21.0* |
| 10 | $N^{LEU}$-((p-CHLOROPHENYL)-THIOCARBAMOYL)-$N^{DISACC}$-(p-PHENOXYBENZYL)A82846B | 1944.3 | 3 | 26.9* |
| 11 | $N^{LEU}$-((p-METHOXYPHENYL)-THIOCARBAMOYL)-$N^{DISACC}$-(p-PHENOXYBENZYL)A82846B | 1940.3 | 3 | 26.0* |
| 12 | $N^{LEU}$-((p-CHLOROPHENYL)-THIOCARBAMOYL)-$N^{DISACC}$-(p-CHLOROBENZYL)A82846B | 1887.5 | 4 | 24.8* |
| 13 | $N^{LEU}$-((p-METHOXYPHENYL)-THIOCARBAMOYL)-$N^{DISACC}$-(p-CHLOROBENZYL)A82846B | 1882.5 | 3 | 25.2* |
| 14 | $N^{LEU}$-((p-NITROPHENYL)-THIOCARBAMOYL)A82846B | 1774.0 | 3 | 19.1* |
| 15 | $N^{LEU}$-((p-(DIMETHYLAMINO)PHENYL)THIOCARBAMOYL)A82846B | 1771.4 | 3 | 17.6* |
| 16 | $N^{LEU}$-((p-(BENZYLOXY)PHENYL)-THIOCARBAMOYL)A82846B | 1834.4 | 3 | 23.3* |
| 17 | $N^{LEU}$-((p-n-BUTYLPHENYL)-THIOCARBAMOYL)A82846B | 1784.4 | 3 | 17.0* |
| 18 | $N^{LEU}$-((p-n-BUTYLPHENYL)-THIOCARBAMOYL)-$N^{DISACC}$-(p- | 1966.5 | 3 | 21.4** |

TABLE I-continued

| Ex # | Name | FAB-MS M + X | Analytical HPLC, min |
|---|---|---|---|
| | PHENOXYBENZYL)A82846B | | |
| 19 | $N^{LEU}$-((p-(DIMETHYLAMINO)-PHENYL)THIOCARBAMOYL)-$N^{DISACC}$-(p-PHENOXYBENZYL)A82846B | 1953.3    3 | 17.1** |
| 20 | $N^{LEU}$-((p-(BENZYLOXY)PHENYL)-THIOCARBAMOYL)-$N^{DISACC}$-(p-PHENOXYBENZYL)A82846B | 2016.3    3 | 21.1** |
| 21 | $N^{LEU}$-(PHENYLTHIOCARBAMOYL)-$N^{DISACC}$-(p-n-BUTYLBENZYL)-A82846B | 1874.6    3 | 19.0** |
| 22 | $N^{LEU}$-(PHENYLTHIOCARBAMOYL)-$N^{DISACC}$-(p-(p-CHLOROPHENYL)-BENZYL)A82846B | 1928.5    3 | 20.3** |
| 23 | $N^{LEU}$-(PHENYLCARBAMOYL)A82846B | 1712.1    3 | 13.8** |
| 24 | $N^{LEU}$-(PHENYLCARBAMOYL)-$N^{DISACC}$-(p-PHENOXYBENZYL)A82846B | 1894.2    3 | 18.9** |
| 25 | $N^{LEU}$-(n-DECYLTHIOCARBAMOYL)-A82846B | 1792.4    3 | N.A. |

*Waters $C_{18}$ Nova-Pak column
**Waters $C_{18}$ μBondapak

The compounds of the present invention are useful for the treatment of bacterial infections. Therefore, in another embodiment, the present invention is directed to a method for controlling a bacterial infection in a host animal, typically a warm-blooded animal, which comprises administering to the host animal an effective, antibacterial amount of a compound of the present invention. In this embodiment, the compounds can be used to control and treat infections due to various bacteria, but especially gram-positive bacteria. In a preferred embodiment, the compounds are used to control and treat infections due to bacteria resistant to existing antibacterials. For example, certain bacteria are resistant to methicillin, and yet others are resistant to vancomycin and/or teicoplanin. The present compounds provide a technique for controlling and treating infections due to such resistant bacterial species.

In carrying out this embodiment of the invention, the compounds of the present invention can be administered by any of the conventional techniques, including the oral route and parenteral routes such as intravenous and intramuscular. The amount of compound to be employed is not critical and will vary depending on the particular compound employed, the route of administration, the severity of the infection, the interval between dosings, and other factors known to those skilled in the art. In general, a dose of from about 0.5 to about 100 mg/kg will be effective; and in many situations, lesser doses of from about 0.5 to about 50 mg/kg will be effective. A compound of the present invention can be administered in a single dose, but in the known manner of antibacterial therapy, a compound of the present invention is typically administered repeatedly over a period of time, such as a matter of days or weeks, to ensure control of the bacterial infection.

Also in accordance with known antibacterial therapy, a compound of the present invention is typically formulated for convenient delivery of the requisite dose. Therefore, in another embodiment, the present invention is directed to a pharmaceutical formulation comprising a compound of the present invention, in combination with a pharmaceutically-acceptable carrier. Such carriers are well known for both oral and parenteral routes of delivery. In general, a formulation will comprise a compound of the present invention in a concentration of from about 0.1 to about 90% by weight, and often from about 1.0 to about 3%.

The antibacterial efficacy of the present compounds is illustrated by Table II. The minimal inhibitory concentrations (MICs) were determined using a standard broth microdilution assay.

TABLE II

Antibacterial Activity, Minimal Inhibitory Concentration (MIC) Against Various Organisms*

| Ex # | RESISTANT | SENSITIVE | SA 446 | SA 489 | SA 447 | SH 105 | SH 415 | SE 270 | SPY C203 | SPN P1 |
|---|---|---|---|---|---|---|---|---|---|---|
| 1 | >128 | 16 | 8 | 4 | 8 | 64 | >64 | 8 | 2 | 2 |
| 2 | 128 | 3.4 | 2 | 2 | 2 | 8 | 16 | 4 | 0.125 | 0.25 |
| 3 | 16 | 1.7 | 4 | 2 | 1 | 2 | 2 | 1 | ≦.06 | |
| 4 | 14 | 4 | 2 | 0.125 | 1 | 2 | 1 | 0.5 | ≦0.06 | 0.125 |
| 5 | >128 | 9.5 | 8 | >64 | 8 | 64 | >64 | 32 | 0.5 | 1 |
| 6 | 128 | 5 | 2 | 16 | 4 | 4 | 8 | 64 | ≦0.06 | ≦0.06 |
| 7 | 19 | 3 | 4 | 2 | 1 | 4 | 2 | 0.5 | 0.25 | ≦0.06 |
| 8 | >128 | 8 | 2 | 2 | 4 | 16 | 64 | 8 | | |
| 9 | >128 | 21 | 8 | 4 | 8 | 32 | 32 | 16 | | |
| 10 | 9.5 | 1.7 | 4 | 2 | 2 | 1 | 2 | 2 | | |
| 11 | 38 | 2.6 | 4 | 2 | 2 | 1 | 2 | 2 | | |
| 12 | 128 | 3.5 | 4 | 1 | 1 | 2 | 4 | 1 | ≦0.06 | ≦0.06 |

TABLE II-continued

Antibacterial Activity, Minimal Inhibitory Concentration (MIC) Against Various Organisms*

| 13 | >128 | 3.5  | 4 | 2   | 2  | 4    | 8   | 2   | ≦0.06 | ≦0.06 |
|----|------|------|---|-----|----|------|-----|-----|-------|-------|
| 14 | >128 | 3.5  | 2 | 2   | 4  | 16   | 32  | 4   | ≦0.06 | 0.25  |
| 15 | >128 | 24   | 8 | 4   | 16 | >64  | >64 | 16  | 0.25  | 0.25  |
| 16 | >128 | 7    | 1 | 0.5 | 1  | 8    | 64  | 4   | ≦0.06 | 0.125 |
| 17 | >128 | 6.1  | 2 | 1   | 1  | 4    | 32  | 2   | 0.25  | ≦0.06 |
| 18 | 4.7  | 1.7  | 2 | 2   | 2  | 2    | 2   | 2   | 0.25  | 2     |
| 19 | 19   | 2.6  | 2 | 2   | 2  | 2    | 4   | 2   | 0.25  | 2     |
| 20 | 9.5  | 5.6  | 4 | 2   | 2  | 2    | 2   | 1   | ≦0.06 | 4     |
| 21 | 32   | 2.6  |   |     |    |      |     |     |       |       |
| 22 | 6.7  | 2.6  | 2 | 1   | 1  | 1    | 2   | 0.5 | ≦.06  | ≦.06  |
| 23 | >128 | 5.3  | 4 | 1   | 4  | 0.5  | 64  | 4   |       |       |
| 24 | 16   | 0.87 | 2 | 1   | 1  | 0.25 | 1   | 1   |       |       |

| ABBREVIATIONS | ORGANISM |
|---|---|
| RESISTANT | *Enterococcus faecium* and *faecalis* (geometric mean of 4–6 isolates) |
| SENSITIVE | *Enterococcus faecium* and *faecalis* (geometric mean of 4–6 isolates) |
| SA446 | *Staphylococcus aureus* 446 |
| SA489 | *Staphylococcus aureus* 489 |
| SA447 | *Staphylococcus aureus* 447 |
| SH 105 | *Staphylococcus haemolyticus* 105 |
| SH 415 | *Staphylococcus haemolyticus* 415 |
| SE 270 | *Staphylococcus epidermidis* 270 |
| SPY C203 | *Streptococcus pyogenes* C203 |
| SPN P1 | *Streptococcus pneumoniae* P1 |

The $N^{LEU}$-thiocarbamoyl compounds of the present invention can also be employed as starting materials to other antibacterial compounds. This use is illustrated by the following reaction sequence:

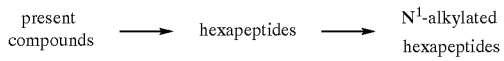

Thus, a present compound is treated with an organic acid, preferably trifluoroacetic acid, in a non-polar solvent, and at a temperature of from about 0° C. to 35° C. This treatment, the second step of an Edman degradation, results in the loss of the leucine group including the thiocarbamoyl substituent. The resulting "hexapeptides" exhibit antibacterial activity and can be employed as described above for the present compounds.

The hexapeptide can thereafter be reductively alkylated to introduce an alkyl group on the amine freed up by the preceding process, the "$N^1$" a amine. Alkylation is achieved by reacting the hexapeptide with an aldehyde to form a Schiff's base, which is then reduced to obtain the $N^1$-alkylhexapeptide. Both reactions are carried out in a polar solvent, such as DMF, and at temperatures of 0–100° C., preferably 60–70° C. The preferred reducing agent is sodium cyanoborohydride. In one embodiment, the reducing agent is added at the same time as the hexapeptide and aldehyde. The resulting $N^1$-alkylated hexapeptides are useful as antibacterials and can be employed as described above for compounds of the present invention.

I claim:
1. A compound of the formula

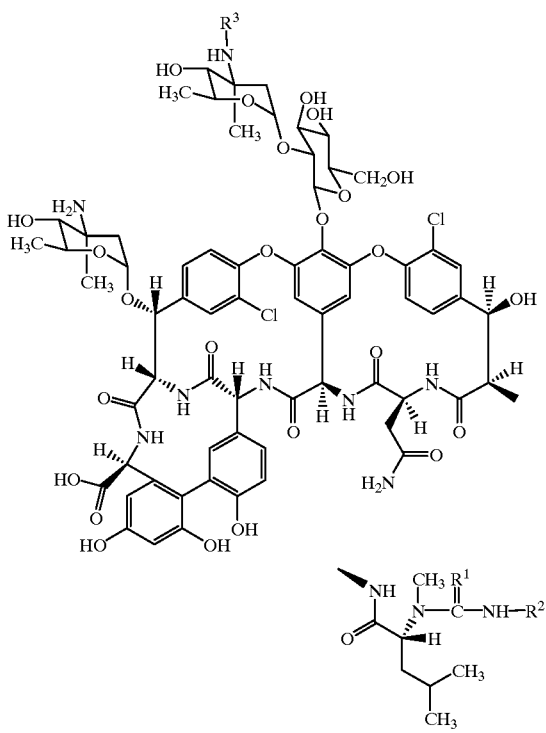

wherein $R^1$ represents O or S;
$R^2$ represents
   alkyl of $C_1$–$C_{10}$,
   phenyl,
   naphthyl, or phenyl substituted by one or two substituents, each of which is independently halo, loweralkyl of $C_1$–$C_4$, loweralkoxy of $C_1$–$C_4$, benzyloxy, nitro, or

wherein each $R^{2a}$ is independently loweralkyl of $C_1$–$C_4$; and $R^3$ represents hydrogen or —$CH_2$—$R^{3a}$ wherein $R^{3a}$ represents
alkyl of $C_1$–$C_{11}$,
alkyl of $C_1$–$C_{11}$—$R^4$, or
$R^4$-$(O_{(0\ or\ 1)}$—$R^4)_{0\ or\ 1}$,
wherein each $R^4$ is independently phenyl or phenyl substituted by one or two substituents, each of which is independently halo, loweralkyl of $C_1$–$C_4$, loweralkoxy of $C_1$–$C_4$, or loweralkylthio of $C_1$–$C_4$, or a pharmaceutically acceptable salt thereof.

2. A compound of claim 1 in which $R^1$ is S.
3. A compound of claim 1 in which $R^2$ is phenyl.
4. A Compound of claim 1 in which $R^3$ is —$CH_2$—$R^{3a}$.
5. A compound of claim 1 in which $R^3$ is p-(p-chlorophenyl)benzyl.
6. A pharmaceutical formulation comprising a compound of claim 1 in combination with a pharmaceutically-acceptable diluent or carrier.
7. A method of treating a bacterial infection in a host comprising the step of administering to the host an effective amount of a formulation of claim 6.
8. A method of claim 7 wherein the bacterial infection is attributable to a vancomycin-resistant-enterococcus.
9. A process for the preparation of a compound as claimed in claim 1 which comprises reacting a parent glycopeptide of the formula

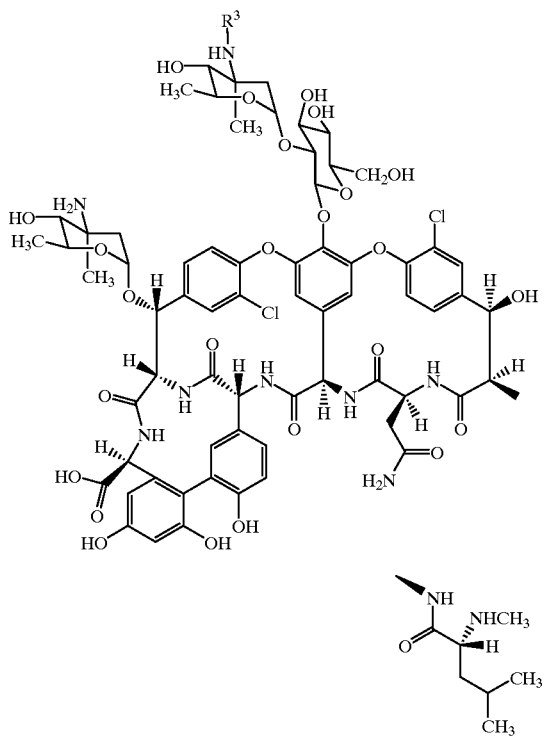

wherein $R^3$ is as defined in claim 1, with an isocyanate or isothiocyanate of the formula $R^1CN$—$R^2$ wherein $R^1$ and $R^2$ are as defined in claim 1, and optionally forming a pharmaceutically acceptable salt.

* * * * *